United States Patent [19]

Weinberg et al.

[11] 4,361,539

[45] Nov. 30, 1982

[54] ANALYSIS SYSTEM

[75] Inventors: Melvin S. Weinberg, Nashua, N.H.; Alan D. Cormier, Newburyport, Mass.

[73] Assignee: Instrumentation Laboratory Inc., Lexington, Mass.

[21] Appl. No.: 245,981

[22] Filed: Apr. 2, 1981

Related U.S. Application Data

[63] Continuation-in-part of Ser. No. 146,705, May 5, 1980, abandoned.

[51] Int. Cl.³ .......................................... G01N 27/30
[52] U.S. Cl. .................................. 422/68; 204/195 B; 422/98
[58] Field of Search ............... 422/68, 80, 81, 98, 422/61, 70; 23/928; 204/195 B, 195 F, 195 P

[56] References Cited

U.S. PATENT DOCUMENTS

| | | | |
|---|---|---|---|
| 3,522,725 | 8/1970 | Waters | 422/70 X |
| 3,640,267 | 2/1972 | Hurtig et al. | 422/68 |
| 3,648,159 | 3/1972 | Stansell et al. | 23/928 X |
| 3,672,843 | 6/1972 | Rosse et al. | 422/68 |
| 3,763,422 | 10/1973 | MacPhee et al. | 422/68 X |
| 3,811,841 | 5/1974 | Kassel | 422/81 |
| 3,811,842 | 5/1974 | Diebler et al. | 422/81 X |
| 3,884,640 | 5/1975 | Lock et al. | 422/68 |
| 3,960,498 | 6/1976 | Zindler et al. | 204/195 P X |
| 3,963,440 | 6/1976 | Stein et al. | 204/195 P X |
| 4,017,374 | 4/1977 | Aas et al. | 204/195 P |
| 4,086,061 | 4/1978 | Hoffa et al. | 422/68 |
| 4,160,714 | 7/1979 | Andersen et al. | 204/195 P |
| 4,202,747 | 5/1980 | Buzza et al. | 204/195 P X |
| 4,207,394 | 6/1980 | Aldridge et al. | 422/61 X |
| 4,221,567 | 9/1980 | Clark et al. | 23/230 B |

FOREIGN PATENT DOCUMENTS

| | | |
|---|---|---|
| 2848073 | 5/1979 | Fed. Rep. of Germany ........ 23/928 |
| 1047138 | 11/1966 | United Kingdom . |
| 1068661 | 5/1967 | United Kingdom . |
| 1084079 | 9/1967 | United Kingdom . |
| 1346533 | 2/1974 | United Kingdom . |
| 1535361 | 12/1978 | United Kingdom . |
| 1558818 | 1/1980 | United Kingdom . |

Primary Examiner—Kenneth M. Schor

[57] ABSTRACT

An analysis system for measuring a plurality of parameters of a fluid sample comprises a housing, and a flow-through cell in the housing that has opposed surfaces with at least two ports in each surface. One of the ports is an inlet port, a second of the ports is an outlet port, and at least two of the ports are sensing ports. A sample flow path including a serpentine portion in the cell serially connects the ports and extends from a port in one surface to a port in the other surface and back to a port in the one surface, and a sensor is disposed in sealing engagement with each sensing port and forms a portion of the serpentine flow path so that sample fluid to be analyzed contacts a surface of each sensor.

16 Claims, 18 Drawing Figures

ANALYSIS SYSTEM

This application is a continuation-in-part of U.S. Ser. No. 146,705 filed May 5, 1980, now abandoned.

This invention relates to apparatus for the analysis of fluid samples and has particular application to apparatus for the analysis of parameters of precious fluids such as blood.

Frequently, an accurate measurement of two or more constituents of a fluid sample of small volume is desired. For example the values of particular constituents of a blood sample may be useful in providing diagnostic information or for the control of life support devices. In particular instances, pH, $pCO_2$, and $pO_2$ values of blood specimens provide important clinical information, and analysis systems employing electrochemical electrodes have been developed for such analysis. Examples of such blood analysis systems are shown in Spergel U.S. Pat. No. 3,658,478 and Zindler U.S. Pat. No. 3,961,498. In such systems, the fluid to be analyzed must be brought to and maintained at a desired stable measuring temperature as the measurement electrode systems in such systems are temperature sensitive. For example blood samples to be analyzed are frequently refrigerated. Exposure of electrode assemblies to different calibrating media or to different temperatures or to reference electrolyte materials may degrade the response of the sensing electrode.

In accordance with the invention there is provided a fluid analysis system that provides improved performance in terms of sample size, accuracy, and precision with a constant temperature environment for the measuring electrodes, sampling cuvette and ancillary components.

In accordance with one aspect of the invention, there is provided an analysis system for measuring a plurality of parameters of a fluid sample that comprises a housing, with a flow-through cell in the housing. The flow-through cell has opposed faces with at least one sensing cavity in each face. A sample flow path includes a serpentine portion in the flow-through cell that serially connects the sensing cavities and extends from an inlet port to a cavity in one surface, then to a sensing cavity in the opposite surface and then to an outlet port. The portion of the serpentine flow path connecting the two sensing cavities in a straight passage segment that extends from the top of one sensing cavity to the bottom of the sensing cavity in the opposed surface. A sensor is disposed in sealing engagement with each face with a bulb-type projection disposed with the sensing cavity to provide an analysis chamber in which the fluid sample to be analyzed flows over the bulb-type projection. Preferably the opposed cell faces are planar and spaced less than five centimeters apart, and the volume of the serpentine flow path between the inlet and outlet ports is less than two hundred microliters. The system provides a small sample volume arrangement that permits accurate measurement of two or more constituents of the sample to be analyzed.

In accordance with another aspect of the invention, there is provided an analysis system for measuring a parameter of a fluid sample that includes a flow-through cell with a generally vertically extending face. A sensing cavity of generally hemispherical configuration has a port in that face and a sensing electrode is seated against the face of the flow-through cell with a bulb-like sensing projection in the hemispherical sensing cavity to define a sensing chamber. The sensing chamber has an inlet port at the bottom and an inlet passage slopes upwardly to the inlet port, and an outlet port at the top of the chamber has an outlet passage sloping upwardly away from that port. This sample chamber configuration disposes the entire sensitive surface of the sensing electrode (e.g., a pH sensitive glass portion) in the chamber for exposure to the sample with a minimal sample volume in an arrangement which minimizes the tendency to bubble entrapment. In a particular embodiment, the inlet and outlet passages have a diameter of about 0.7 millimeter, the hemispherical cavity has a diameter of less than five millimeters and a depth of less than five millimeters with the end surface of the bulb-like projection spaced less than two millimeters from the end wall of the cavity. The outlet port from the cavity advantageously may be slightly enlarged to enhance optimum flow characteristics and sample integrity in the analysis chamber.

In a particular embodiment, the flow-through cell is of transparent material so that the fluid sample in the serpentine flow path may be visually observed, and the serpentine flow path portion includes a plurality of straight passage segments, each of which extends through the flow-through cell from a hemispherical sensing cavity in one face to a hemispherical sensing cavity in the opposite face, with each passage segment extending from the top of the cavity in one face to the bottom of the cavity in the opposed face, the passage segments being disposed at an angle of at least fifteen degrees to the horizontal. Each passage segment is of capillary dimension (less than one millimeter in diameter), the opposed cell surfaces are planar and spaced less than 1½ centimeters apart, and the volume of the serpentine flow path in the flow cell between the inlet and outlet ports is about 55 microliters that includes fluid control structure which permits selective introduction of calibration fluids into the flow path. That fluid control has a first mode in which the sensing ports are connected in series with the inlet port so that fluid from the same sample may be flowed serially from the inlet port to the sensing ports for concurrent sensing by the sensors, and a second mode in which a first sensing port is in fluid communication with a first calibrating fluid inlet, a second sensing port is in fluid communication with a second calibrating fluid input, and the sensing ports are in fluid isolation from one another so that the sensors may be calibrated concurrently and independently of one another.

In that particular embodiment the flow path in the flow-through cell extends in a generally vertical direction with the sample to be analyzed being flowed upwardly through the flow path by pump means connected to the outlet port and a flush solution being flowed downwardly (in the reverse direction) through the flow path. A reference port in one of the cell surfaces is in communication with the flow path and a crest or loop type of trap portion is provided in the flow path for preventing reference electrolyte from flowing from the reference port to a sensing cavity.

In accordance with another aspect of the invention, there is provided an analysis system for measuring a parameter of a fluid sample that includes two heat sink members with a flow-through cell between them. The flow-through cell has opposed faces and each heat sink member has a surface in mating heat exchange contact with a corresponding face of the cell. A flow passage through the cell has an inlet port, an outlet port, and at least one sensing cavity. Heater structure is provided on each heat sink member for maintaining a stable temperature of the heat sink members and the flow-through cell. A sample analysis electrode extends through a bore in a heat sink member with a sensing tip disposed in sealing engagement in the sensing cavity and forming a portion of the flow path so that the fluid sample to be analyzed contacts the tip surface of the sensor. Preferably the heat sink members are electrically grounded metal blocks with planar surfaces in mating heat exchange contact with corresponding planar opposed cell faces in a sandwich array.

In a particular embodiment, the flow-through cell is of transparent material and a transparent front wall member is seated against the front surfaces of the heat sink members. Two chambers in that front wall member hold calibrating gas conditioning liquids so that the temperature of the conditioning liquids is stabilized at essentially the stable system temperature established by the two heat sink members and permitting flow rates of the calibrating gases to be adjusted by observing bubble rates in the chambers. Flow-through heat exchange structures are mounted on the top and bottom surfaces of the heat sink members for flow of calibrating and flush fluids to bring those fluids to the system temperature as they are flowed into the system. In that particular embodiment, the sample to be analyzed is introduced through a preheater through passage in one of the heat sink blocks in alignment with the inlet port of the flow-through cell. A first sensor is connected to measure a gaseous parameter of the fluid sample at a first sensing cavity, and a second sensor is connected to measure an ionic parameter of the fluid sample at a second sensing cavity, and the fluid control is connected between the first and second sensing cavities.

The system further includes a series of sample detectors disposed at spaced points along the length of the sample path for detecting the presence of sample fluid at spaced points along that path, the sample detectors being components of a sample position sensing system of the electrical conductivity type. In one operational mode, three parameters of a 120 microliter sample are measured concurrently, and in a second operational mode parameters of a 65 microliter sample are measured serially with the sample position being monitored by the sample position detectors.

While a preferred embodiment of the invention is designed for measuring an ionic parameter and partial pressures of gases of blood and blood derivatives, the invention is not limited to blood gas measurements and may be used with other sensing systems.

Other features and advantages will be seen as the following description of a particular embodiment progresses, in conjunction with the drawings, in which.

DESCRIPTION OF PARTICULAR EMBODIMENT

Figure 1:
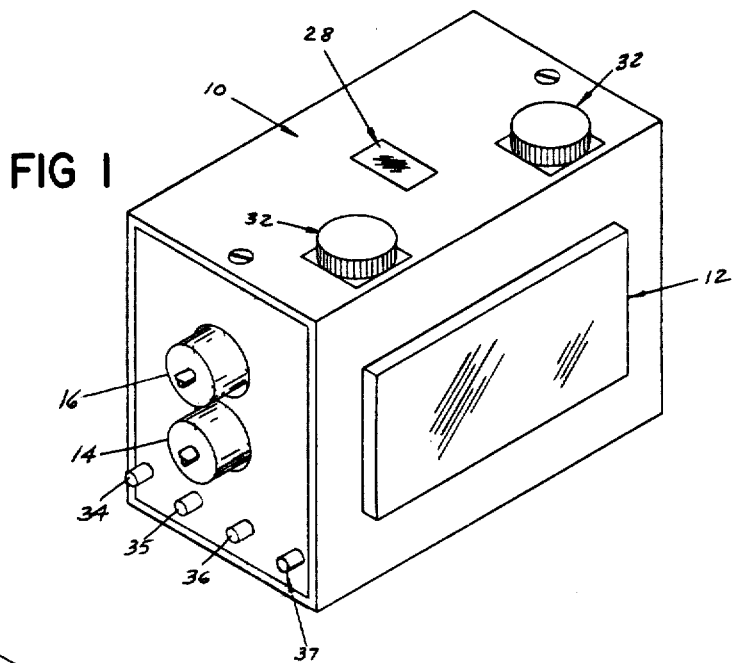
FIG. 1 is a perspective view of a blood gas analysis module in accordance with the invention.
Figure 2:
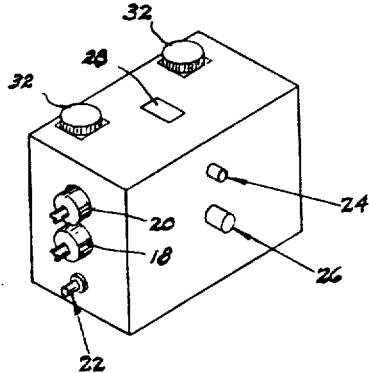
FIG. 2 is a perspective view showing the rear of the module shown in FIG. 1.

A blood gas analysis module for use in a blood gas analysis system in accordance with the invention is shown in FIG. 1. That module includes a housing 10 that has a front viewing window 12 and that receives a $pO_2$ electrode assembly 14 and a pH electrode assembly 16 at one end. As indicated in the rear perspective view of the module in FIG. 2, the housing receives a $pCO_2$ electrode assembly 18 and a reference electrode assembly 20 at the other end. The module has a sample inlet port 22 at one end surface below carbon dioxide assembly 18 and an outlet port 24 in its rear face. A valve shaft 26 also projects from the rear face of the module. In the upper surface of the module is a window 28 for admitting light to the flow-through sample cell 30 within module 10. On either side of viewing window 12 is a chamber that is closed by a fill cap 32 and which contains water for humidifying calibration gases for calibration of each gas electrode. Ports 34, 35, 36, and 37 for connection to sources of calibration fluids are at the left end of the analysis module.

Figure 4:
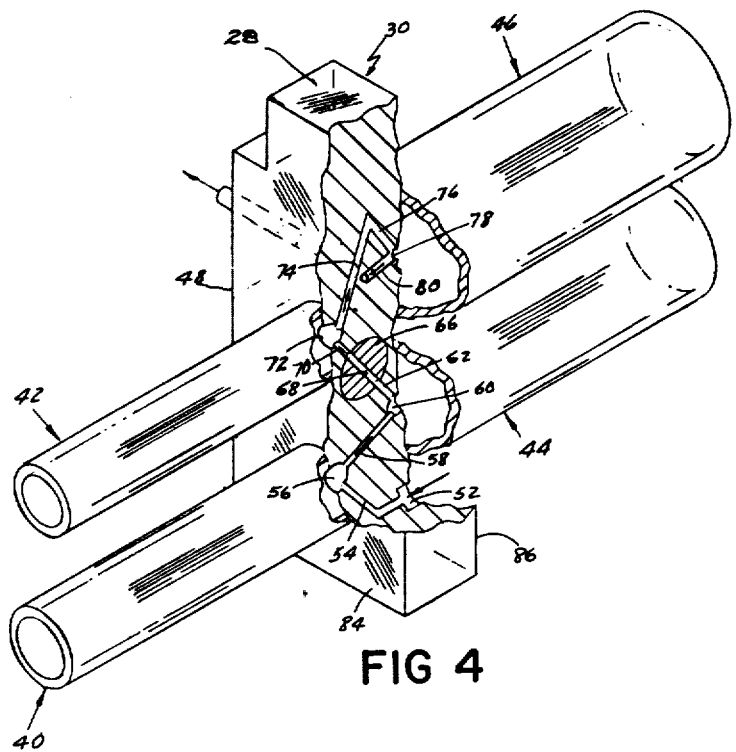
FIG. 4 is a perspective front view of a subassembly of the cell member and electrode sleeves.
Figure 3:
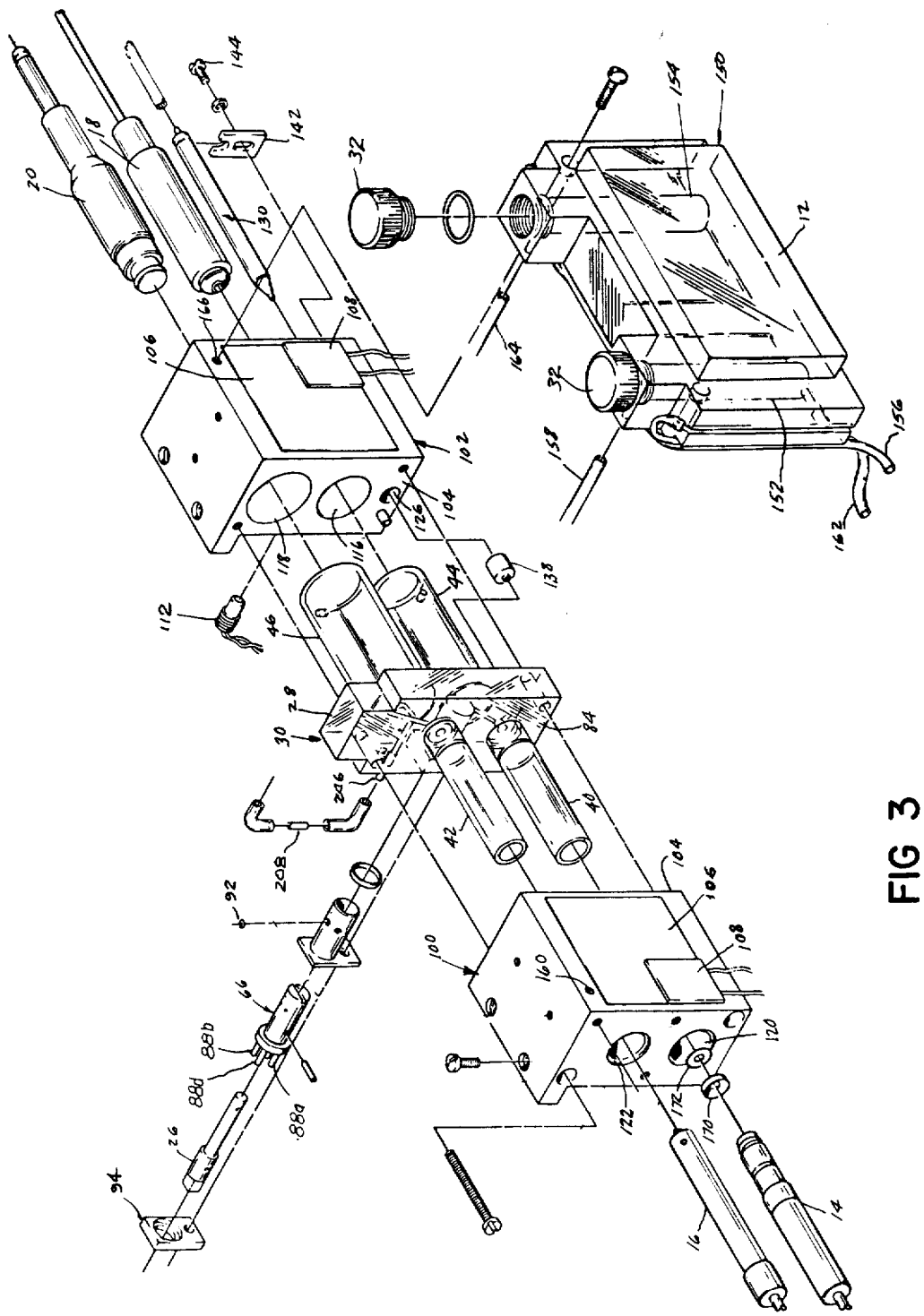
FIG. 3 is an exploded front view of components of the module of FIG. 1.
Figure 5B:
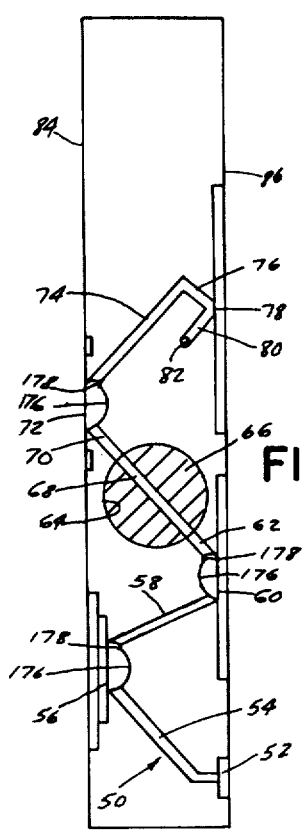
FIG. 5B is a diagrammatic sectional view showing the sample flow path through the cell member.
Figure 5A:
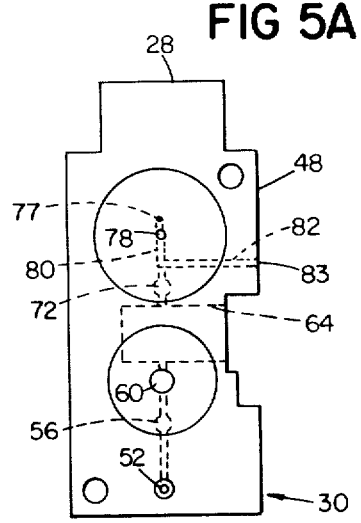
FIG. 5A is a side view of the cell member.

Further details of the analysis module may be seen with reference to FIG. 3. Flow-through cell 30 as fabricated from a clear colorless (acrylic) material and has four sleeves 40, 42, 44, 46 of the same material bonded to the cell body 30 to provide a leakproof unit. The rear surface 48 of cell body 30 has a reflective coating that in combination with the light admitting top window 28 and the wide aperture of viewing window 12 enhances the visibility of the sample to be analyzed in the flow path 50 that extends through cell 30. As indicated in the perspective view of FIG. 4, the side view of FIG. 5A and the diagrammatic sectional view of FIG. 5B, that flow path extends from inlet port 52 of about 0.7 millimeter in diameter through a first passage segment 54 that slopes upwardly at an angle of about 50 degrees to a sensor cavity 56 that has a port diameter of about 2.8 millimeters and a depth of about 1.3 millimeter; through a second passage segment 58 that slopes upwardly at an angle of about 30 degrees to a second sensor cavity 60 that has a port diameter of about four millimeters and a depth of about 2.3 millimeters; through a third passage segment 62 that slopes upwardly at an angle of about 50 degrees to cylindrical chamber 64 which receives flow control valve spool 66 in which is formed a through passage 68; through a passage segment 70 to a third sensor cavity 72 that has a port of about 3.5 millimeter diameter and a depth of about 2.5 millimeter; through passage segments 74 and 76 with a crest 77 at their intersection to a reference electrode port 78 of about 0.8 millimeter in length (the crest 77 at the intersection of passage segments 74 and 76 having a height of about one millimeter above reference port 78); and then through passage segments 80 and 82 to exit port 83 at the rear surface 48 of cell 30. The ports of sensor cavities 56 and 72 open towards planar cell face 84 while ports 60 and 70 open towards opposed planar face 86. The diameter of each passage segment is about 0.7 millimeter; the distance between cell surfaces 84 and 86 is about thirteen millimeters; and the volumetric displacement of the sample flow path between inlet port 52 and exit port 83 at the rear face of cell 30 is about 55 microliters. While various types of fluid control 66 may be utilized, a suitable fluid control is the rotary valve disclosed in copending application Ser. No. 104,296 filed Dec. 17, 1979, and entitled SPOOL VALVE and assigned to the same assignee as this application, the disclosure of which is incorporated herein by reference. As indicated in FIG. 4, the spool 66 of the valve has a through passage 68. Also formed in the spool 66 are for calibration passages 88, two of which are shown in the sectional view of FIG. 6. Each calibration passage 88 extends to a port 90 in the cylindrical surface of spool 66. Each port 90 is sealed by a captivated O-ring 92 and retainer plate 94 is secured with fastener 96.

Figure 7A:
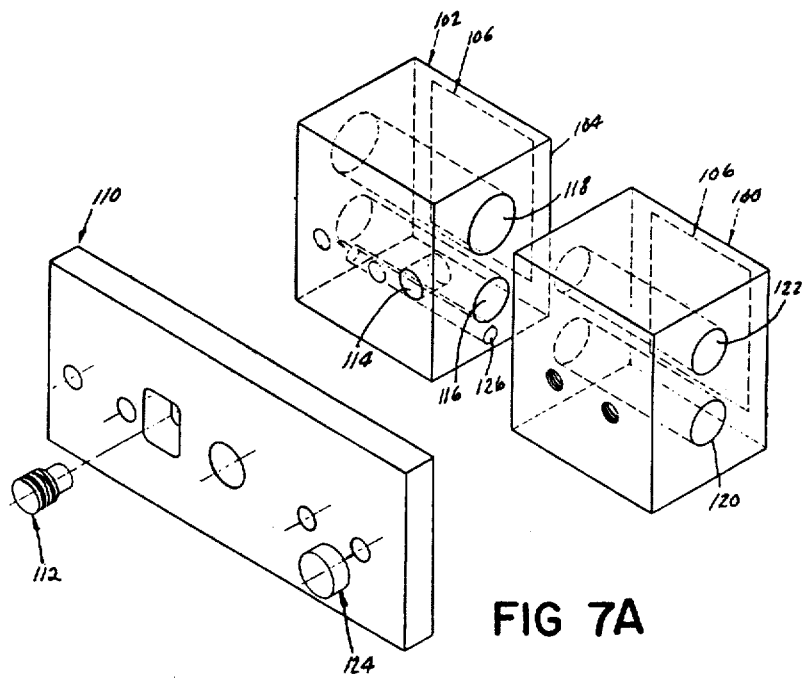
FIG. 7A is an exploded rear view of the heater blocks 100, 102 and assembly plate 110.
Figure 7B:
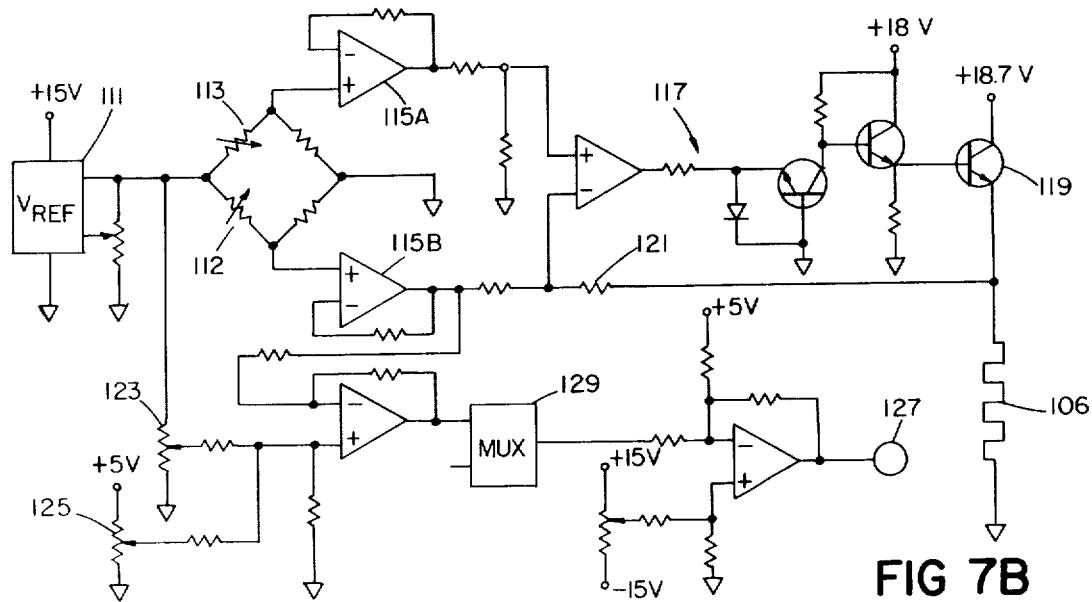
FIG. 7B is a circuit diagram of heater circuitry.

Referring again to FIG. 3, on either side of cell 30 is an aluminum heater block 100, 102, each of which has a planar surface 104 that is clamped in heat transfer engagement with the corresponding planar surfaces 84, 86 of cell 30. Secured to the front surface of each heater block is a heater pad 106 with a terminal connection 108. Common assembly plate 110 as indicated in FIG. 7 is bolted to the rear of heater blocks 100, 102. A temperature control probe 112 is mounted in recess 114 of block 102 between the electrode sleeve bores 116 and 118. Similar electrode sleeve bores 120 and 122 are formed in heater block 100. As indicated in FIG. 7B, sensing thermistor 112 is connected in a bridge circuit 113 to which a regulated voltage is applied from voltage reference circuit 111. Balanced voltage amplifiers 115A, 115B feed current amplifier circuitry 117 to control power transistor 119 which in turn controls the flow of current through heater pads 106. A feedback loop is provided through resistor 121 and a reference is established by coarse adjustment 123 and fine adjustment 125. A temperature monitor 127 is connected to the circuit by electronic switch 129. Heater pads 106 are wired in parallel to the proportional controller which regulates the temperature of the heater blocks 100 and 102, and thermal cutout 124 provides protection against overheating.

Figure 8:
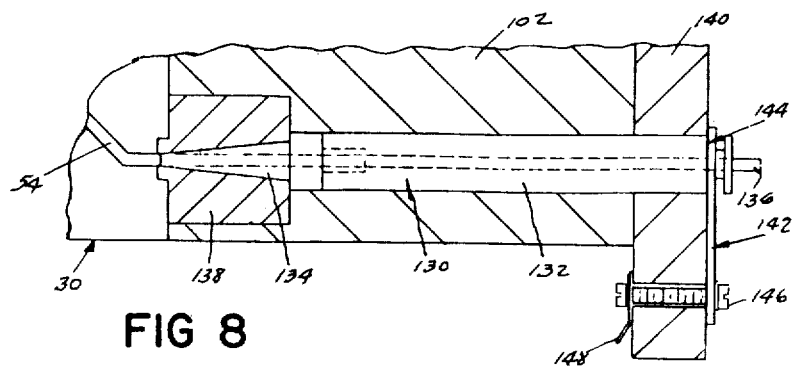
FIG. 8 is a sectional view through a heater block showing details of the sample preheater.

Disposed in bore 126 of heater block 102 (see FIG. 8) is a sample preheater 130 which includes an aluminum sleeve 132, a stainless steel taper fitting 134, and a through stainless steel tube 136. A high electrical resistance epoxy coating on outer surface of aluminum sleeve 132 isolates that sleeve from heater block 102. An elastomer seal 138 is received in heater block 102 and in turn, the tapered end of fitting 134 is seatingly sealed in elastomer seal 138. There is an insulator end plate 140 bolted to the outer end face of each heating block. Clamp plate 142 engages an uncoated surface 144 of heater sleeve 132 and provides an electrical connection through fastener 146 to sensor lead 148 as a component of the electrical conductivity sample position sensing system.

With reference once again to FIG. 3, the front wall of the module includes a clear plastic (acrylic) member 150 in which is formed viewing window 12, on either side of which is a humidifier chamber 152, 154 that is closed by cap 32. Calibration gas from inlet 37 is flowed through conduit 156 into chamber 152 and out through conduit 158 which is disposed in bore 160 of heater block 100. A second calibration gas from inlet 36 is flowed through conduit 162 to humidifier chamber 154 and out through conduit 164 which is disposed in bore 166 of heater block 102. The temperature of the humidifying water in each chamber 152, 154 is maintained at essentially the stable system temperature (as determined by the temperature of heater blocks 100 and 102) as the acrylic member 150 is seated against the front surfaces of the heater blocks, and the gas flow rate through each chamber may be controlled by observation of bubbles through each water reservoir 152, 154.

Figure 10A:
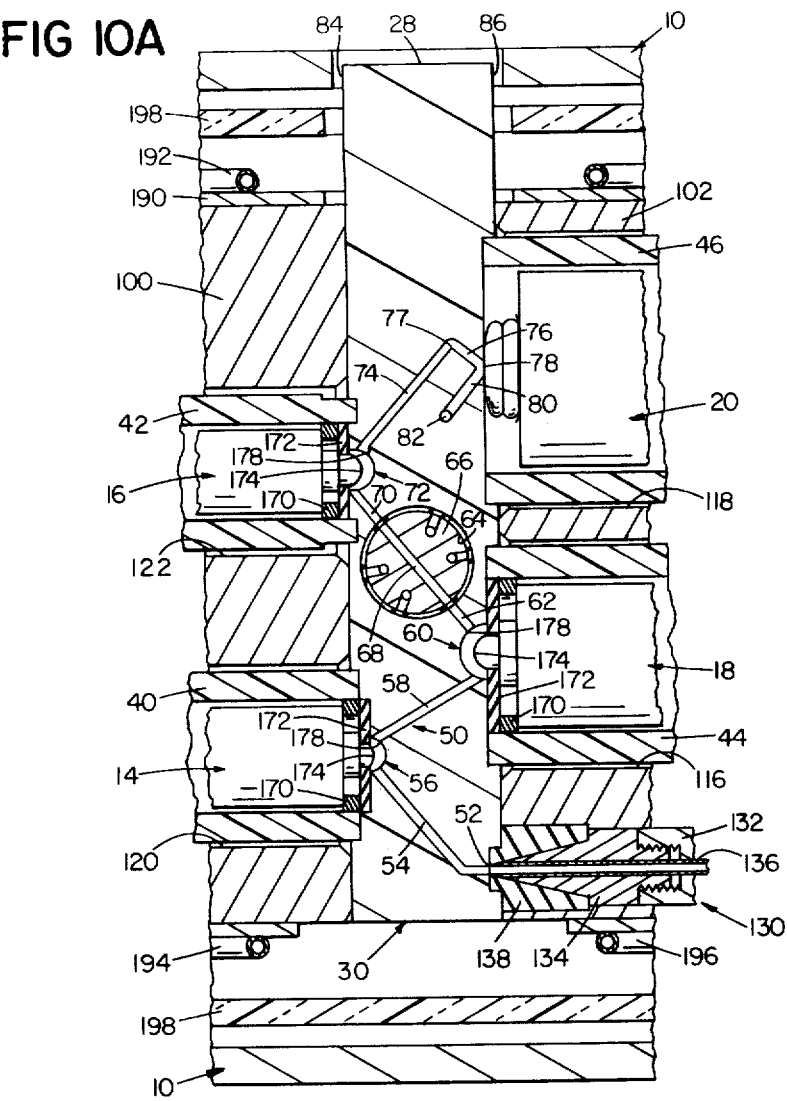
FIG. 10A is a sectional view showing the sample flow path through the cell member.
Figure 10B:
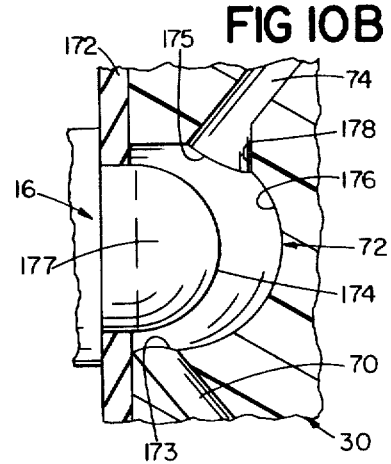
FIG. 10B is an enlarged sectional view of a portion of the sample flow path shown in FIG. 10A.
Figure 9:
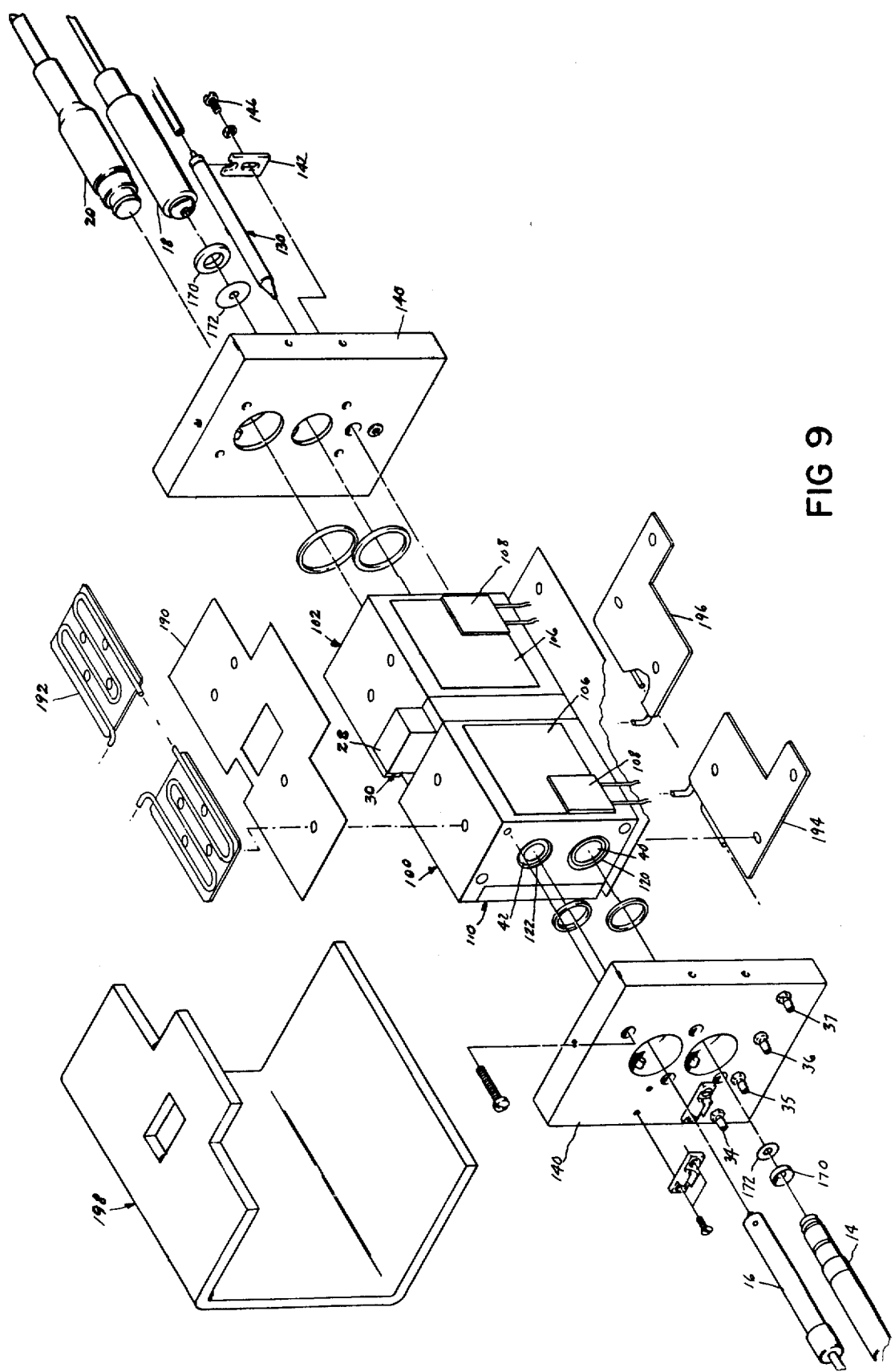
FIG. 9 is an exploded front view of components of the module of FIG. 1 with cell member 30 and heater blocks 100, 102 assemble together.

As indicated in the subassembly shown in FIG. 9, sleeves 40 and 42 are inserted through bores 120 and 122 in heater block 100, and sleeves 44 and 46 are similarly inserted through bores 116 and 118 in heater block 102. As shown in FIG. 10A, the $O_2$ electrode assembly 14, together with retainer 170 and elastomer seal 172 are inserted through sleeve 40 and seated at sensing cavity 56 of cell 30. $CO_2$ electrode assembly 18, pH electrode assembly 16 and reference electrode 20 are similarly seated at cell cavities 60, 72, and 78 respectively. Each bulb-type projection 174 of an electrode assembly is received in its sensing cavity with the seal 172 sealing the cavity. A compression type spring axially loads each electrode to maintain the seal. Each inlet capillary passage segment, as indicated in FIGS. 10A and 10B slopes upwardly and extends to an inlet port 173 at the intersection between the cavity surface 176 and the planar cell face against which seal 172 is seated and each outlet capillary passages slopes upwardly away from an outlet port 175 at the top of the cavity. Each cavity is dimensioned so that the entire pH sensitive portion 177 of the bulb projection 174 is disposed within the sensing cavity and entirely exposed to the sample in the flow path with the periphery of the bulb-like projection 174 spaced about $\frac{1}{4}$ millimeter from the cavity wall and the tip of the bulb-like projection spaced about $1\frac{1}{2}$ millimeters from the base of the cavity. Sample liquid flows upwardly through the flow path around and over the entire sensitive surface 177 of the sensing electrode in an analysis chamber of minimal volume, which together with the sloped capillary passage flow path reduces tendency to trap flush solution or sample within the cavity. The outlet port 175 at the top of each cavity may be enlarged by a groove 178 to further relieve possible entrapment of gases.

Mounted on top of the heat blocks 100, 102 on electrical insulator sheet 190 is a cleaning solution preheater 192; and similar buffer solution preheaters 194, 196 are mounted on the bottom surfaces of blocks 100 and 102, respectively. A fiberglass insulated sleeve 198 is disposed over the top, rear, and bottom walls of this subassembly and is encased in housing 10. Thus the aluminum heat sink blocks 100, 102 which are maintained at 37° C., stabilize the temperature of flow-through cell 30, gas conditioning chambers 152, 154, and preheaters 192, 194 and 196, in a module assembly that is about fifteen centimeters long, about eight centimeters high and about six centimeters deep. Blocks 100, 102 are electrically grounded and provide shielding for electrodes 14, 16, 18, and 20.

Figure 11:
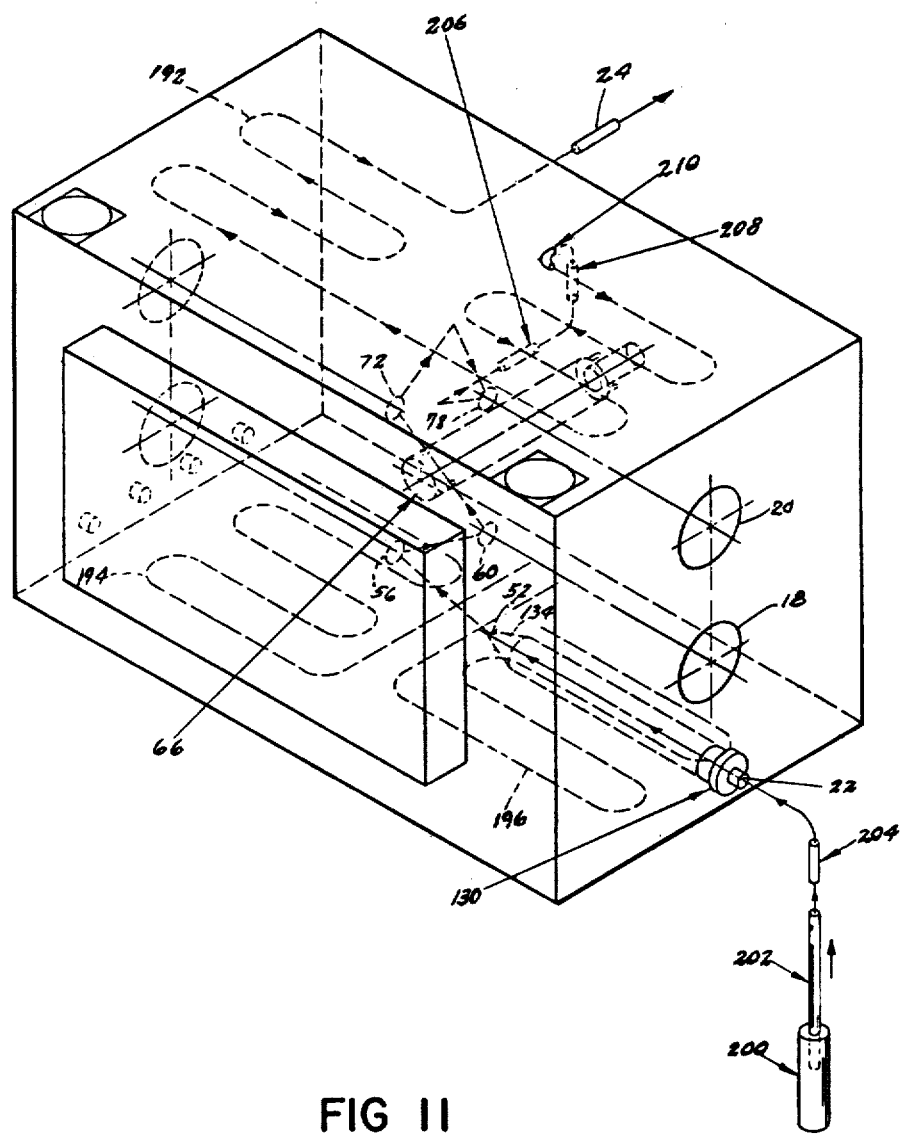
FIG. 11 is a diagrammatic view showing location of position sensors in the sample flow path in the module of FIG. 1.

The sample flow path through the module is indicated in the diagram of FIG. 11. The sample to be analyzed is withdrawn from sampling vessel 200 by sampling needle 202 and flows through a first position sensor 204 to inlet 22 of sample preheater 130. The sample emerges from tapered tip 134 of preheater 130 and flows through the serpentine path of measuring cell 30 from inlet port 52 serially past sensor port 56, sensor port 60, through valve 66, past sensor port 72 and reference port 78, through second position sensor 206 and third position sensor 208 and fourth position sensor 210 into the flush preheater 192 on top of the heater block and then out exit port 24 at the rear of the module. Position sensors 204, 206, 208, and 210 function in a position sensing system that utilizes the electrical conductivity of the sample to complete electrical circuits, in conjunction with the sample preheater 130 and the rotary valve 66. A 210 hertz signal is applied to the sample preheater 130 and to the valve 66 for sample position sensing purposes.

Figure 6:
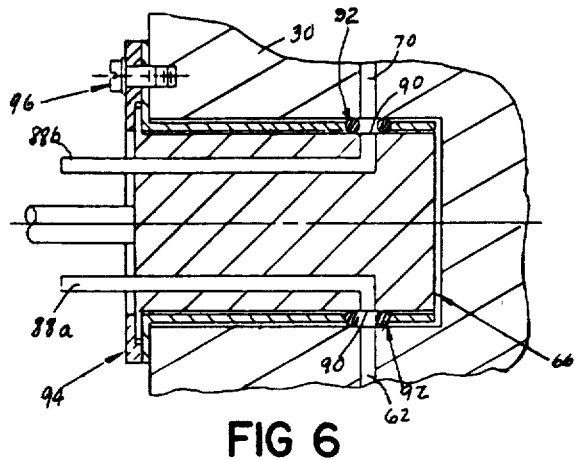
FIG. 6 is a sectional view showing the rotary spool valve 66 in a calibration position.

Flow control valve 66 has three operative positions, an analysis position in which transverse passage 68 through the valve spool is aligned with passage segments 62 and 70; a first calibrating position (as shown in FIG. 6) in which calibration gas from inlet 37 is bubbled through humidifying chamber 152 and then flowed to valve passage 88a in the spool that is connected to passage segment 62 and a buffer liquid from inlet 35 is flowed through preheater 194 and the upper inlet 88b to passage segment 70; and a second calibrating position (with spool 66 rotated through a further 60 degrees angle) in which a calibration gas from inlet 30 is flowed through bubble chamber 154 and port 88c of the spool valve for flow into passage segment 62 and a buffer from inlet 34 is flowed through preheater 196 to valve inlet 88d to passage segment 70.

The sensing module has five operational modes: two calibration modes, two sample analysis modes, (a 65 microliter sample mode and a 120 microliter sample mode), and a flush mode. External microprocessor control selects the appropriate fluid flow patterns for each function.

In the 120 microliter sample analysis mode, rotary valve 66 is indexed to the sample position as shown in FIG. 11. Sampling needle 202 is inserted in sampling vessel 200 and the peristaltic pump connected to exit port 24 is operated to induct about 120 microliters of blood up to preheater 130. The conductivity of the blood sample completes a circuit between the preheater 130 and sampling needle 206, signaling the induction of the sample, and the pump is stopped to allow withdrawal of needle 202 from vessel 200. The pump then advances the sample to valve 66, and the pump is stopped to allow equilibration of the oxygen electrode 14 and the carbon dioxide electrode 18. The pump then advances the 120 microliter sample to sensor 210. Crest 77 provides electrolyte isolation between reference electrode 20 and pH electrode 16. After the blood sample to be analyzed has been so flowed and located concurrently at the three sensor ports and the reference port, data translating circuits are released and measurements of pH, $pCO_2$, and $pO_2$ are simultaneously obtained.

Figure 12:
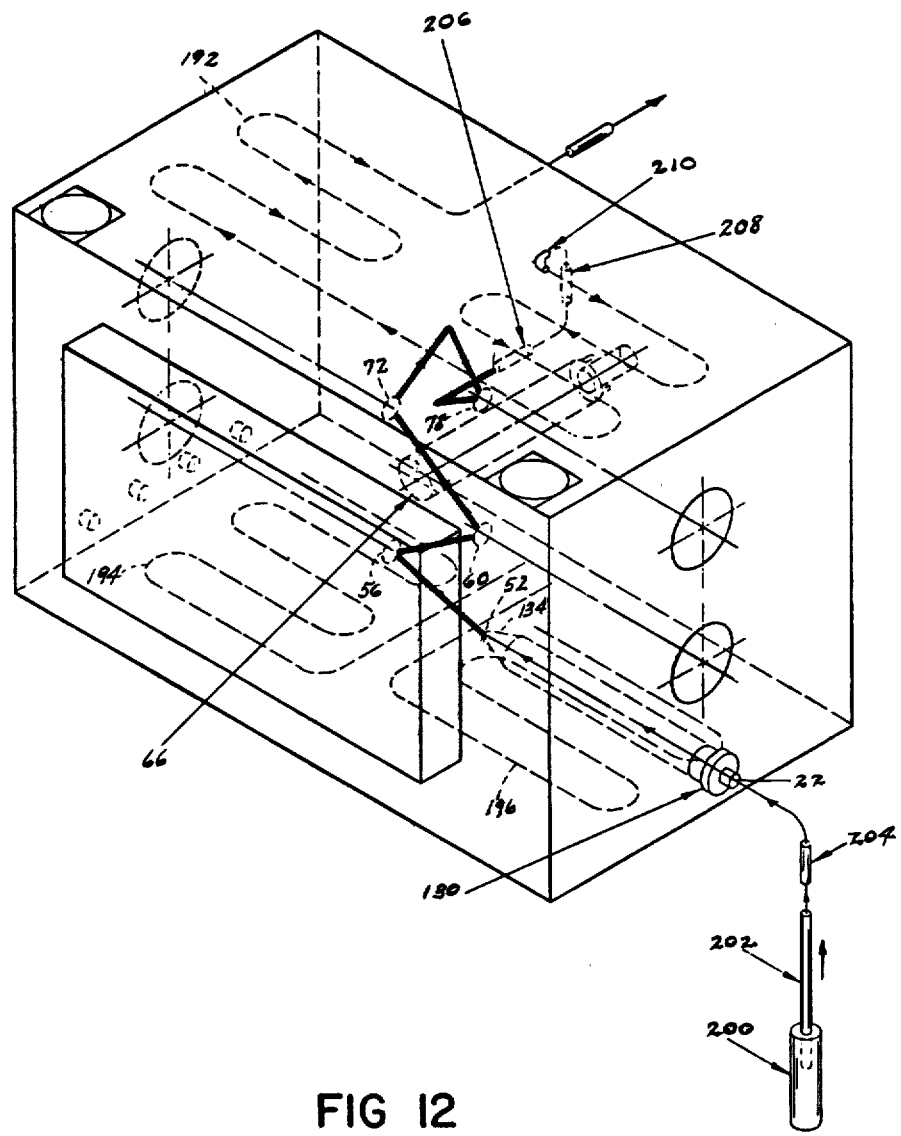
FIGS. 12 and 13 are diagrammatic views similar to FIG. 11 showing two locations of a smaller sample (65 microliter volume) for analysis.
Figure 13:
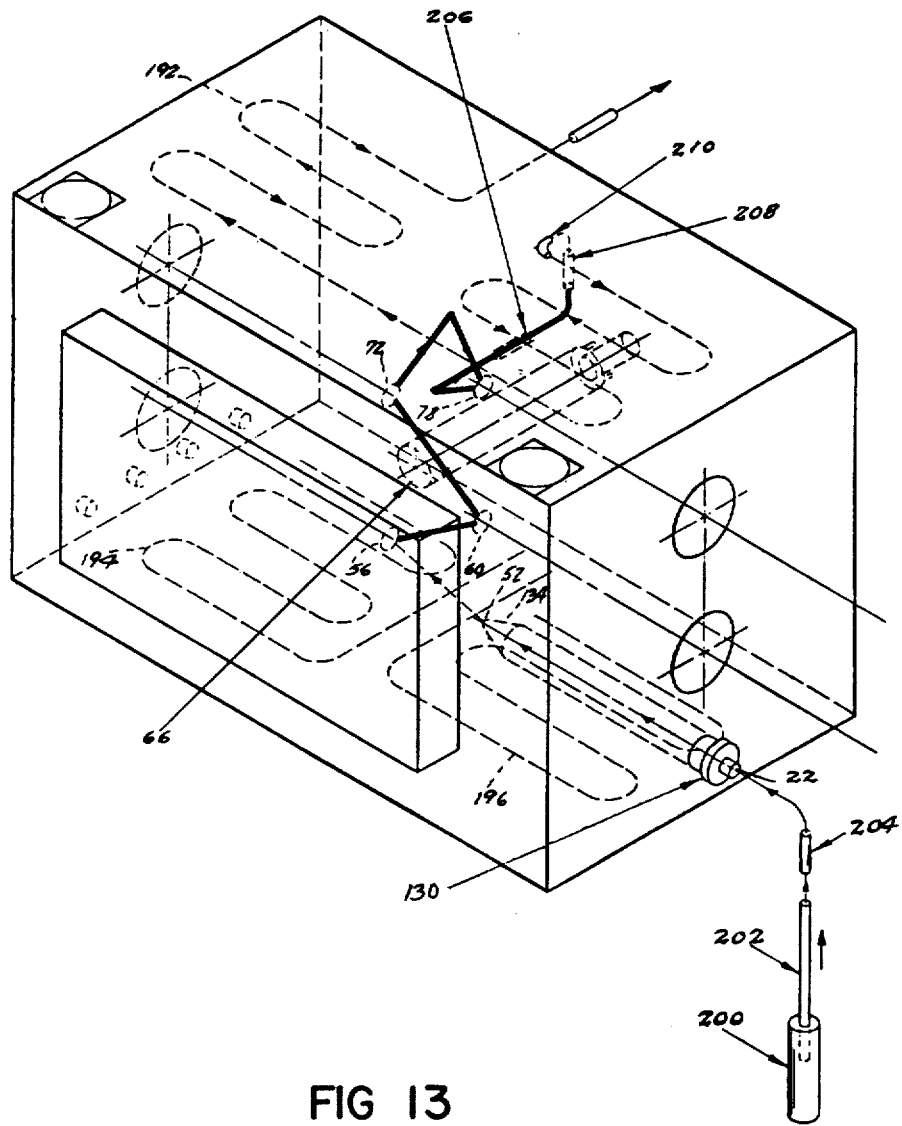

When it is desired to analyze a smaller (65 microliter) sample volume, the sample to be analyzed is inducted only to sensor 204 and then the sampling needle is withdrawn from the sampling vessel. The sample is first advanced through preheater 130 to the sensor 206 (FIG. 12) where there is a pause for equilibration of the carbon dioxide and pH electrodes. At this time the data translating circuit for the oxygen electrode 14 is released and a $pO_2$ measurement on the microsample is made. The sample is then advanced to sensor 208 (to the position shown in FIG. 13) and pH and carbon dioxide measurements are made. After the measurements have been completed, the sample is flushed from the module.

Figure 14:
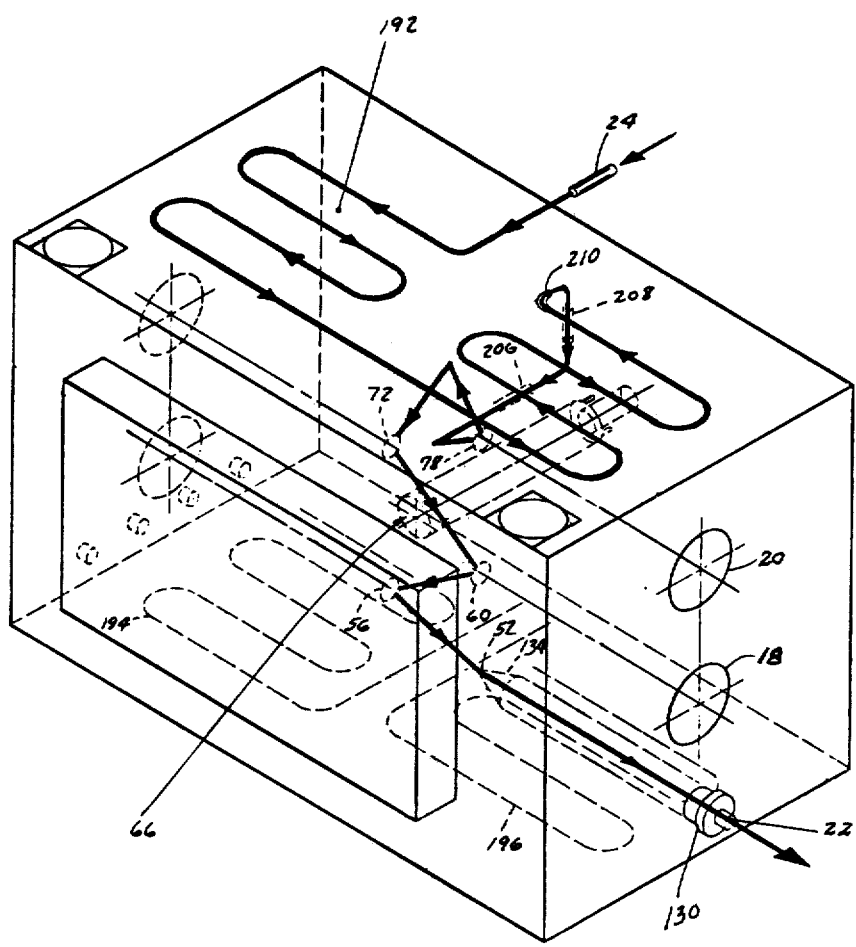
FIG. 14 is a diagram similar to FIG. 11 showing the flush flow path.

The flush cycle flow path is shown in FIG. 14. In the flush cycle, flow control valve 66 remains in the sample position, and cleaning is accomplished by back flushing the system under pressure with flush solution being pumped through flush preheater 192 and the serpentine passage in cell 30 and through preheater 130 and the sampling needle 202 to waste along the path as indicated in FIG. 14.

Figure 15:
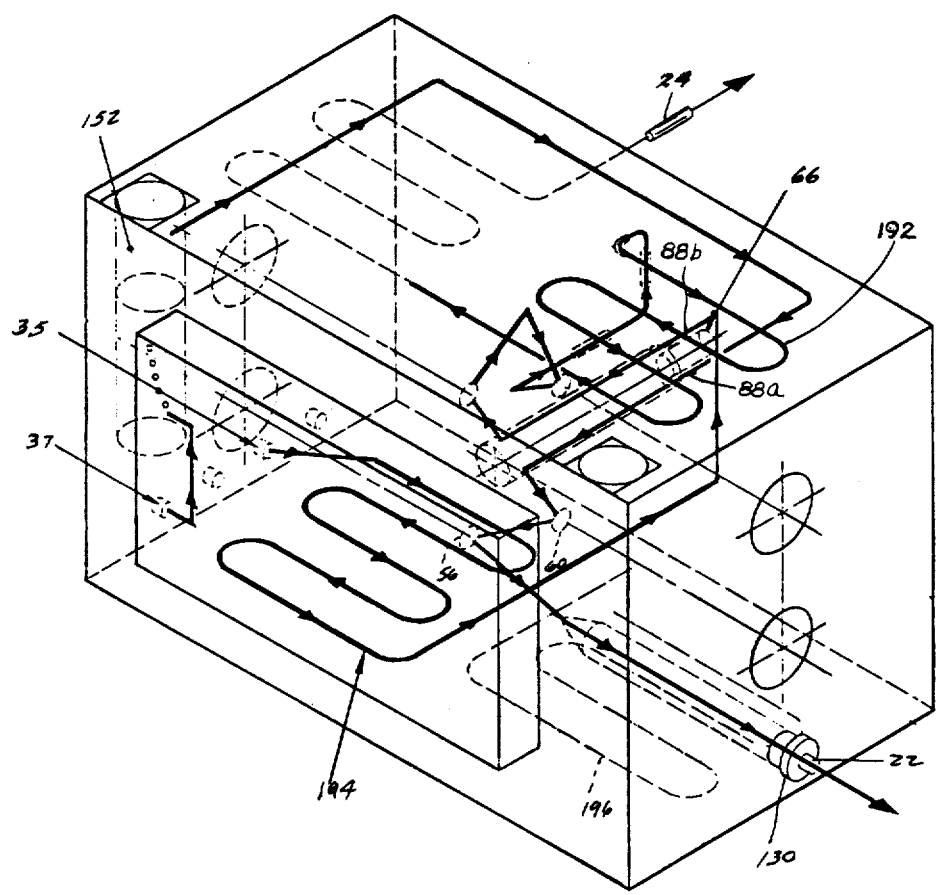
FIG. 15 is a diagram similar to FIG. 11 showing the flow path of calibration fluids in one of the calibration modes.

The flow path in a calibration mode indicated in FIG. 15. For calibration, rotary valve 66 is indexed (rotated 60 degrees) to a first calibration position and then indexed a further 60 degrees to a second calibration position. In each calibration position, a calibration gas bubble chamber is connected to an inlet of valve 66 and the calibration gas is humidified by bubbling through the bubble chamber and then flows through the valve into passage segment 62 and past sensor ports 60 and 56 and out sample preheater. At the same time a buffer solution is pumped by the aspiration pump connected to the exit port 24 through the selected buffer preheater and valve passage to passage segment 70 for flow past sensing port 72 and reference port 78.

While a particular embodiment of the invention has been shown and described, various modifications will be apparent to those skilled in the art, and therefore it is not intended that the invention be limited to the disclosed embodiment or to details thereof and departures may be made therefrom within the spirit and scope of the invention.

What is claimed is:

1. An analysis system for measuring a plurality of parameters of a fluid sample comprising:
   a housing,
   a flow-through cell in said housing, with structure in said cell defining an inlet port, an outlet port, and at least two sensor accepting ports, said cell having opposed faces and an annular sealing surface surrounding each said sensor accepting port, with at least one sensor accepting port in each face,
   structure in said cell defining a sensing cavity of generally hemispherical configuration behind each said sensor accepting port,
   means defining a sample flow path including a serpentine portion in said cell, said flow path serially connecting said inlet port, said sensing cavities and said outlet port, and including a straight passage segment extending from a sensing cavity in one face to a sensing cavity in the other face, and
   a sensor disposed in sealing engagement with each said sensing cavity and forming a portion of said sample flow path so that sample fluid to be analyzed contacts a surface of each said sensor,
   each said sensor having a bulb-like sensing projection and each said sensor being seated against a said face of said flow-through cell with its bulb-like sensing projection in a said hemispherical sensing cavity to define a sensing chamber, each said sensing chamber having a cavity inlet port at the bottom with an inlet passage portion of said sample flow-path sloping upwardly to said cavity inlet port, and a cavity outlet port at the top of said chamber with an outlet passage portion of said sample flow-path sloping upwardly away from said cavity outlet port.

2. The system of claim 1 wherein said hemispherical cavity has a depth of less than five millimeters, and a diameter of less than five millimeters, and the end surface of said bulb-like projection structure is spaced less than two millimeters from the face of said hemispherical cavity.

3. The system of claim 1 wherein said cavity inlet port is located immediately adjacent said face of said flow-through cell and is less than one millimeter in width.

4. The system of claim 1 and further including a fluid control in said serpentine portion in said cell, said fluid control having a first mode in which said sensing ports are connected in series with said inlet port so that fluid from the same sample may be flowed serially from said inlet port to said sensing ports for concurrent sensing by said sensors, and a second mode in which a first sensing port is in fluid communication with a first calibrating fluid inlet, a second sensing port is in fluid communication with a second calibrating fluid inlet, and said sensing ports are in fluid isolation from one another so that said sensors may be calibrated concurrently and independently of one another.

5. The system of claim 1 wherein a first sensor is connected to measure a gaseous parameter of the fluid sample at a first sensing port, and a second sensor is connected to measure an ionic parameter of the fluid sample at a second sensing port, said inlet port is connected to said first sensing port and a fluid control is connected between said first and second sensing ports.

6. The system of claim 1 and further including a reference port in one of said cell surfaces in communication with said serpentine path, said serpentine portion having a trap portion for preventing reference electrolyte from flowing from said reference port to a sensing port.

7. The system of claim 1 wherein said flow-through cell is of transparent material so that fluid sample in said flow path may be visually observed.

8. The system of claim 7 wherein said system includes a light transmitting window in the front wall of the housing for transmitting light to said flow-through cell.

9. The system of claim 1 and further including a series of sample detectors disposed at spaced points along the length of said serpentine path for detecting the presence of sample fluid at spaced points along said path.

10. The system of claim 9 wherein said plurality of sample detectors are components of a sample position sensing system of the electrical conductivity type.

11. The system of claim 1 wherein each said passage segment is of capillary dimension (less than one millimeter in diameter), said opposed cell surfaces are planar and spaced less than five centimeters apart.

12. The system of claim 1 wherein the volume of said flow path between said inlet and outlet ports is less than two hundred microliters.

13. The system of claim 1 wherein said serpentine flow path in said flow-through cell extends in a generally vertical direction and further including means to flow the sample to be analyzed upwardly through said serpentine flow path.

14. The system of claim 13 wherein said sample flow means includes pump means connected to said outlet port, and further including means to flow a flush solution downwardly through said serpentine flow path.

15. The system of claim 14 and further including a reference port in one of said cell surfaces in communication with said serpentine path, said serpentine path having a crest portion for preventing reference electrolyte from flowing from said reference port downwardly to a sensing cavity.

16. The system of claim 1 wherein said flow-through cell is of transparent material so that fluid sample in said flow path may be visually observed, said housing has a transparent front wall portion that includes window structure for viewing said flow-through cell, and said transparent front wall portion includes chamber structure for storing conditioning liquid through which a sensor calibrating gas is bubbled.

* * * * *